US012623095B2

(12) United States Patent
Vilkomerson

(10) Patent No.: US 12,623,095 B2
(45) Date of Patent: May 12, 2026

(54) SYSTEM AND METHOD FOR VOLUME INSONATION

(71) Applicant: DVX LLC, Princeton, NJ (US)

(72) Inventor: David Vilkomerson, Princeton, NJ (US)

(73) Assignee: DVX LLC, Princeton, NJ (US)

( * ) Notice: Subject to any disclaimer, the term of this patent is extended or adjusted under 35 U.S.C. 154(b) by 0 days.

(21) Appl. No.: 19/170,420

(22) Filed: Apr. 4, 2025

(65) Prior Publication Data

US 2025/0312624 A1     Oct. 9, 2025

Related U.S. Application Data

(60) Provisional application No. 63/661,407, filed on Jun. 18, 2024, provisional application No. 63/575,806, filed on Apr. 7, 2024.

(51) Int. Cl.
*A61N 7/02*     (2006.01)
*A61N 7/00*     (2006.01)
(52) U.S. Cl.
CPC ........ *A61N 7/02* (2013.01); *A61N 2007/0021* (2013.01); *A61N 2007/0078* (2013.01)
(58) Field of Classification Search
CPC .............. A61N 7/02; A61N 2007/0021; A61N 2007/0078
See application file for complete search history.

(56) References Cited

U.S. PATENT DOCUMENTS

| | | | | |
|---|---|---|---|---|
| 2008/0304362 A1* | 12/2008 | Fleming | ................. | H04B 13/02 |
| | | | | 367/134 |
| 2014/0276050 A1* | 9/2014 | Jenson | ..................... | A61N 7/00 |
| | | | | 600/439 |
| 2015/0135836 A1* | 5/2015 | Rose | ...................... | G01N 29/04 |
| | | | | 73/597 |
| 2015/0257779 A1* | 9/2015 | Sinelnikov | ............. | A61N 7/022 |
| | | | | 606/28 |
| 2016/0374710 A1* | 12/2016 | Sinelnikov | ......... | A61B 17/3207 |
| | | | | 600/439 |
| 2019/0353572 A1* | 11/2019 | Ning | ....................... | G01P 5/241 |

* cited by examiner

*Primary Examiner* — Hien N Nguyen
(74) *Attorney, Agent, or Firm* — Princeton IP Law LLC

(57)     ABSTRACT

In an embodiment, a method for providing insonation volume in ultrasound therapy treating tissues, e.g., brain tissues, at a target region includes: using a catheter to introduce a linear transducer array into a body lumen to be near the brain tissues to be treated; causing to determine an operating frequency and a length of the linear transducer array to be excited, based at least in part on the attenuation coefficient of the brain tissues and the distance of the target region from the catheter; and causing to excite the length of the linear transducer with a signal at the operating frequency to produce ultrasound intensity in a volume between a self-focusing point and the linear transducer array, wherein the ultrasound intensity in the volume is between a maximum intensity and half of the maximum intensity. The linear transducer array may include a plurality of ring transducer segments.

24 Claims, 12 Drawing Sheets

SYSTEM AND METHOD FOR VOLUME INSONATION

RELATED APPLICATIONS

This application claims the benefit under 35 U.S.C. § 119 (e) of U.S. Provisional Application No. 63/575,806, filed Apr. 7, 2024 and U.S. Provisional Application No. 63/661, 407, filed Jun. 18, 2024. The entire contents of these applications are incorporated herein by reference.

FIELD

This technology relates to using ultrasound energy for therapeutic purposes, and more particularly to techniques for volume insonation of ultrasound.

BACKGROUND

There is increasing interest in using ultrasound energy for advanced therapeutic purposes. Ultrasound diathermy has been used for decades to heat joint and muscle tissues for pain and soreness relief. More recently, techniques of focused ultrasound (FUS) that allow for precise ablation of certain brain areas with high-intensity sound waves, in combination with MRI imaging, have shown to be effective for treatment in the brain to, for example, reduce or eliminate essential tremor.

Other ultrasound techniques exist that use low-intensity ultrasound in conjunction with microbubbles to open the blood-brain-barrier. The blood-brain-barrier ("BBB") prevents drugs whose molecular size exceed about 400 Daltons from passing from the blood into the brain, preventing most drugs from being effective therapy for neurodegenerative conditions, e.g. Alzheimer disease, amyotrophic lateral sclerosis (ALS), Parkinson disease and brain tumors. Opening the blood-brain-barrier has been achieved by ultrasound applied through the skull (with correction for the skull's distorting of the beam) to a desired area where it interacts with infused microbubbles to open the BBB.

In these techniques that utilize microbubbles, the intensity of the insonation is controlled to avoid "inertial cavitation," which is when the oscillating acoustic pressure is so high that it causes the microbubbles to overexpand and then collapse, releasing so much energy that it injures nearby tissue. "Stable cavitation" uses lower pressures where the bubbles expand and contract continuously with the acoustic field and affect the vessel walls to open the BBB, allowing drugs to enter brain tissue. The range of acoustic intensity between undesired inertial cavitation and the desired stable cavitation is understood to be approximately two-to-one. This range of acoustic pressure is referred herein as the therapeutic range.

BRIEF DESCRIPTION OF DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

DETAILED DESCRIPTION

Figure 1:
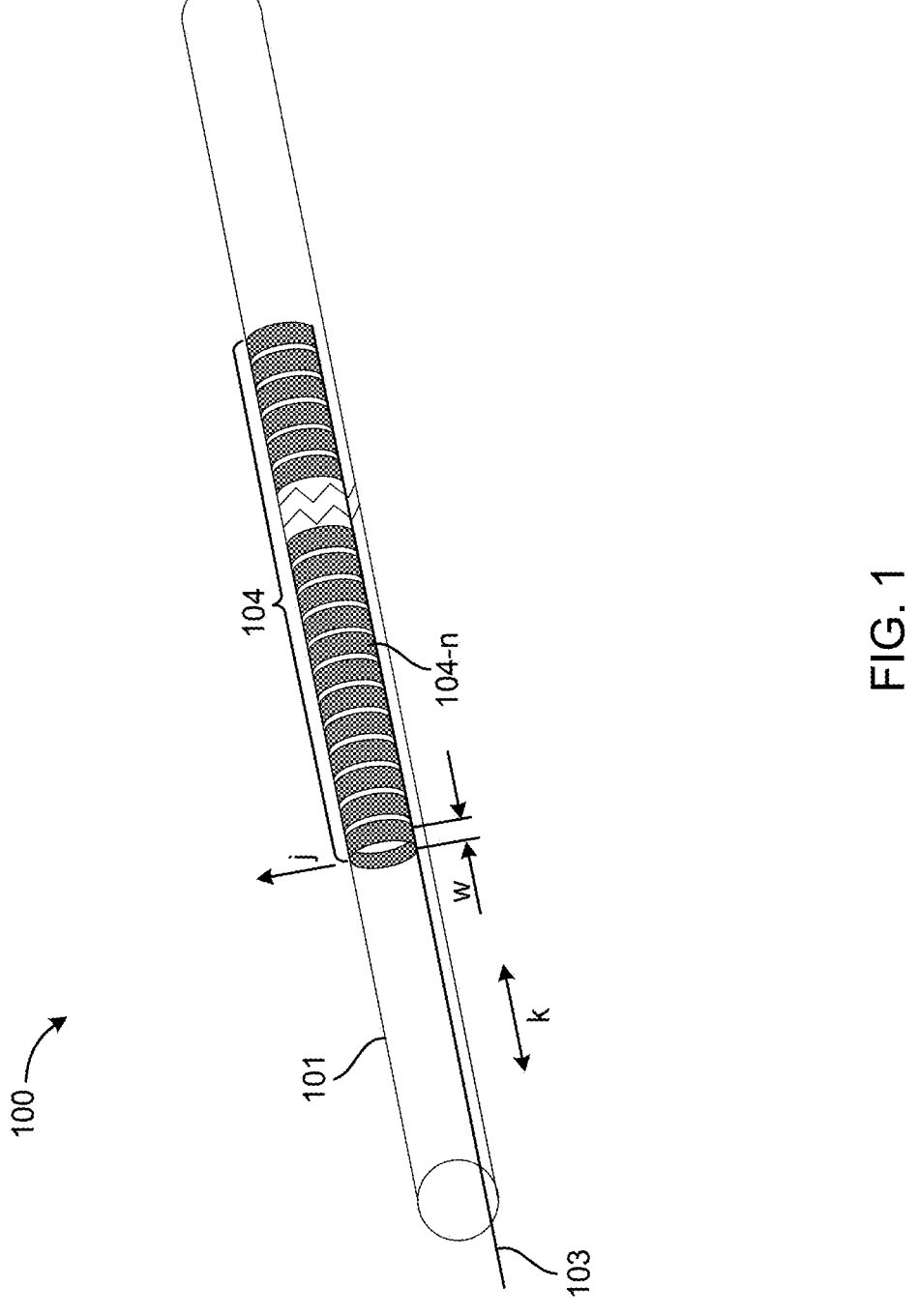
FIG. 1 is a schematic diagram of an example device used for producing large volume insonation, according to some embodiments. The ring transducers in a linear array of ring transducers as shown emit wavefronts equivalent to a point source at their center.

In the field of ultrasound therapy treating tissues, e.g., brain tissues, existing techniques generally use transcranial focused ultrasound, such as focused ultrasound equipment being sold by Exablate. The ultrasound device is placed on the skull and produces focused beams on the targeted tissue using MRI to monitor the beam position.

The inventors have recognized and acknowledged that in these existing focused ultrasound systems, each focal targeted volume is very small. Demonstration of the effectiveness of ultrasound and microbubbles ("US+MB") in human brains has been shown using large concave arrays of transducers focusing through the skull into the brain. The volume of brain tissue where the BBB is opened ("BBBO") in existing transcranial devices per excitation is where the therapeutic range is achieved: the area of the half-intensity diameter of the acoustic focal spot multiplied by the half-intensity length of focus, which is less than 1 milliliter (mL). As the brain volume is about 1400 mL, it requires thousands of focused ultrasound regions to treat even a small portion of the brain. As a result, many hours of treatment are required, making clinical use extremely difficult and expensive.

Accordingly, the inventors have developed techniques to produce large volumes of quasi-uniform ultrasound, e.g., in the therapeutic range of intensities for BBBO, intracranially. For the important use of an acoustic fields for opening the blood-brain barrier, previous research employed focused ultrasound and showed safe BBB-opening occurred over a two-to-one range of acoustic intensity. In the present disclosure, a useful part of the array's insonated volume is where the intensity lies between the maximum in the total acoustic field and one-half of that maximum—the therapeutic range.

Techniques are provided that produce ultrasound pressures in therapeutic range in volumes hundreds of times larger than existing transcranial methods. For example, a transducer shown in FIG. 1 includes a thin and flexible linear transducer array disposed along an axial direction of a catheter. The transducer array includes an array of rotationally symmetric ring transducers for producing cylindrical, rotationally symmetric field with large volumes of therapeutic intensity ultrasound in the brain, providing clinically useful methods of BBBO.

These techniques utilize the fact that the circulatory system in the brain includes veins that connect to the jugular vein which can be easily accessed at the neck. Interventional radiologists have developed skills at passing catheters through the circulatory system and can introduce catheters into the brain veins from the jugular vein. The catheter can be inserted into the lumen (e.g., a circulatory system) of a subject and moved therethrough to address tissue to be insonated. In some embodiments, a catheter using this device may require a single driving-signal cable for the transducer array, allowing such a catheter to be thin and flexible (compared with conventional focusing ultrasound arrays that require multiple drive cables). Diffractive effects, "constructive interference", is used to produce a self focus in what is known as the "near field". The energy concentrating effect of focusing (as used with a "burning glass") balances the ultrasound tissue attenuation so that a large volume of effective therapeutic level ultrasound can be attained between the catheter and the self focus region.

In some embodiments, the width of each of the transducers in the transducer array and the spacing between the transducers may be configured based on the frequency of the driving signal and the tissue in the propagating path in order to achieve a particular level of ultrasound intensity in the insonated volume. In some embodiments, the transducer array may be shifted spatially (e.g., by moving the catheter) while being excited by a driven signal to cause overlaps of insonation intensity so that any holes (under-intensity) regions) in the insonation intensity can be filled, resulting in quasi-uniform intensity in the "near field" (proximate in space around the transducer array). In some embodiments, the transducer array may be driven by selective excitation pulses electronically. For example, the transducers in the transducer array may be arranged such that two groups of the transducers are excited alternately for selective excitation.

In other embodiments, the array of transducers may include an array of segments-of-ring transducers, e.g., partially wrapped around the catheter. This configuration may achieve a partial cylindrical-shaped insonation volume that is fan-shaped along the axial direction of the catheter but affecting only the tissue facing those segments.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended. It should be further appreciated that the embodiments described herein may be implemented in any of numerous ways. Examples of specific implementations are provided below for illustrative and didactic purposes only. It should be appreciated that these embodiments and the features/capabilities provided may be used individually, all together, or in any combination of two or more, as aspects of the technology described herein are not limited in this respect.

FIG. 1 is a schematic diagram of an example device having a linear array of transducers, according to some embodiments. A transducer device 100 may include a sequence of ultrasound ring transducers 104 arranged in a transducer array. The transducers 104 may be arranged in parallel, each comprising a thin segment, e.g., 104-n. In some embodiments, the transducer array 104 may be disposed on a catheter 101. The catheter 101 may be used to carry the transducer array 104 to inside a body through a body lumen or remove the same out of the body. In some embodiments, the transducer array 104 may be disposed on the catheter with each transducer segment (e.g., 104-n) being fully wrapped around the circumference of the shaft of the catheter for form a ring. For example, the transducer may be a plastic film transducer, which can conform to the round shape of the shaft of the catheter. Various methods may be used to attach a transducer array to a catheter. For example, piezoplastic material may be dip-coated onto the catheter and then electroded and poled to form the ring array. Alternatively, the transducers can be made individually and then fastened onto the catheter and interconnected.

In some embodiments, the transducer segments (e.g., 104-n) in transducer array 104 may be energized in parallel via a driving device. In some examples, the driving device may be a cable 103, e.g., a coax cable carried within the catheter wall, a microstrip printed on the catheter, or other such suitable device for energizing ultrasound transducers. Parallel driving of these array elements in the transducer, rather than individually driving the array elements with phase-controlled signal as in conventional focused ultrasound arrays. enables a thin flexible catheter or other carrying device to be used. Although catheter is described as an example, it is appreciated that in some variations, the transducer array 104 may be disposed on other devices, such as a trocar or any suitable carrier device, e.g., long, flexible, thin element.

The transducer array may be fabricated in any of the varieties known in the field or later developed. For example, ultrasound transducer array 104 may include small piezoelectric elements, such as PZT, or MEMS, such as CMUT or PMUT, or of piezoplastics, such as PVDF or P (VDF-TrFE).

In some embodiments, the ultrasound field produced by the parallel-driven transducers in transducer array 104 can be calculated by Huygens-Fresnel theory, appropriate to the "near field": the acoustic amplitude measured in space around and in proximity of the transducer array is the sum of the wavefronts from n point sources (e.g., the centers of the ring transducers) at frequency f and wavelength $\lambda$ in the tissue, propagating through tissue of attenuation constant $\alpha$ (e.g. $\alpha=0.004$/MHz/mm for brain tissue) as calculated by Equation (1):

$$A_{x,r} = \sum_{n=0}^{n=last} \left(\frac{T_n}{d}\right) 10^{-\alpha f d} \cos b \, e^{-\frac{i 2 \pi d}{\lambda}} \qquad (1)$$

where d is the distance between the nth transducer center and the observation point at (x,r), b is the obliquity angle between the transducer point-transmitter and the observation point, $\lambda$ is the wavelength of the driving signal. Eq. (1) represents summing the contribution of all the transmitters of amplitude $T_n$ of frequency f and wavelength $\lambda$, in tissue that attenuates at a rate of $10^{\alpha f}$ propagating through tissue a distance d at an angle b, which gives the acoustic amplitude at observation point (x,r). By repeating this calculation for every point in space around the array, the acoustic intensity (ultrasound intensity) $A^2$ in the insonated volume, can be calculated.

Figure 2A:
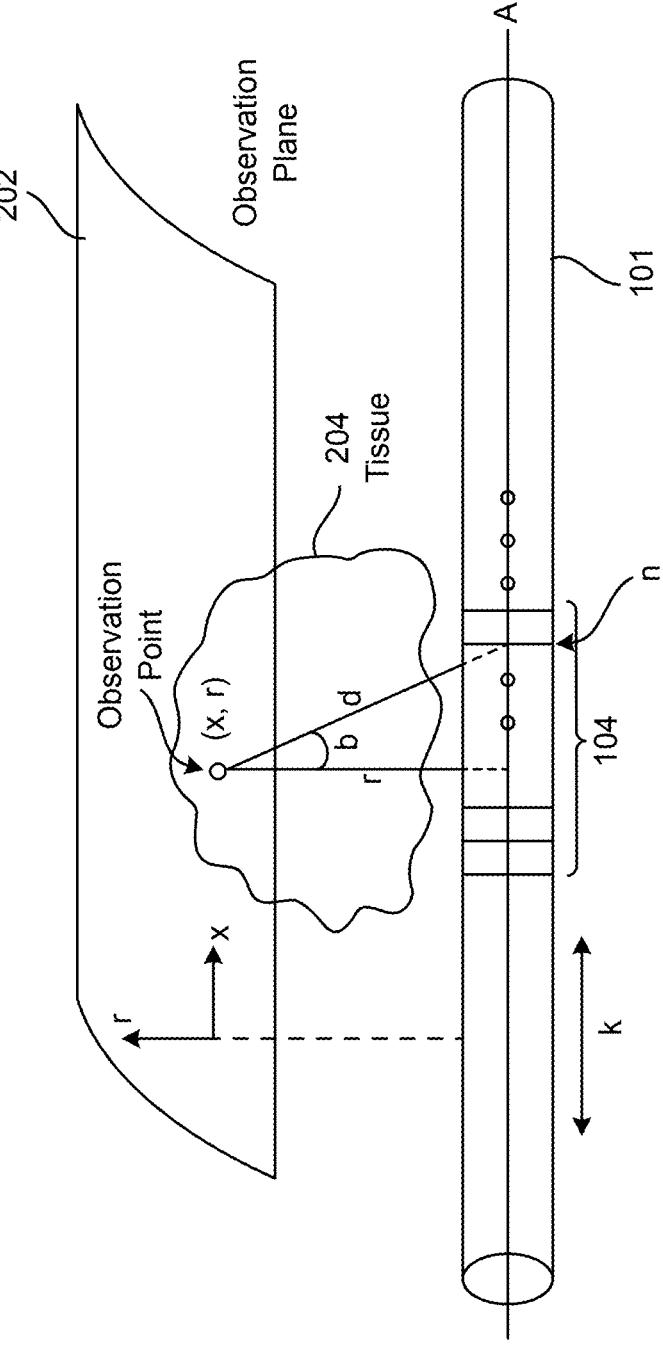
FIG. 2A illustrates an observation plane and observation point relative to a point source in the transducer array of the device in FIG. 1, according to some embodiments.

FIG. 2A illustrates an observation plane and observation point relative to a point source n in the transducer array of the device in FIG. 1, according to some embodiments. In FIG. 2A, an observation point (x, r) is on an observation plane 202 at a distance r from the catheter 101 (e.g., an axial line of the catheter shown as A), where the observation plane 202 is a cylinder surrounding the transducer array (a portion of which is shown). In the above calculation in Eq. (1), the distance d extends from the center of transducer segment n to the observation point (x, r) on the observation plane 202, and cos(b) is r/d. In the configuration shown, the center of the transducer segment is also on the axial line of the catheter. In these examples, the x-axis extends in an axial direction along the transducer array; and the r-axis extends radially away from the catheter (e.g., axial line of the catheter).

For use close to these transducers (e.g., inside the body near the blood vessel in which the catheter is inserted), the "near field" theory holds. In the "near field" zone, there is a maximum in intensity and minimum in beam width ("self-focus") along the perpendicular to the center of the array at a distance directly proportional to the length of the array squared, and inversely proportional to the wavelength (i.e., proportional to the frequency). The length of the array is the total length of the array along the axial direction of the catheter. For example, the length of the array $L_A$ is the sum of the width of the transducer segments in the transducer array energized and the sum of spacings among them. In non-limiting examples, the self-focus distance from the transducer array is proportional to the length of the array driven squared, $L_A^2$, and inversely proportional to the wavelength of the ultrasound in the tissue 204.

In some embodiments, the acoustic field in insonated tissue produced by a linear array of transducers (see 100 in FIG. 1) being driven in parallel can be determined using Eq. (1), with adjusting the length of the array, its operating frequency, and the attenuation of the tissue to calculate the approximate insonating volume produced.

Returning to FIGS. 1 and 2A, Eq. (1) is valid for point-like ultrasound transmission. For example, in non-limiting examples, the width of individual transducer segments 104-n, w, along the axial direction k of the catheter may be small relative to the wavelength (e.g., 0.1). If more energy is desired, wider transducers up to the limit of half a wavelength may be used. In such case, amplitude $T_n$ in Eq. (1) may be scaled by a factor based on the limited angular range of emitted ultrasound from a transducer of width w, as known from classical diffraction theory of a slit that the emitted amplitude at an angle $\theta$ is $\text{sinc}[\pi(w/\lambda)b]$: therefore for point-like emission, $w/\lambda$ is desired to be small; so the width should be $<\lambda*\frac{3}{4}$ and center-to-center spacing of the transducer elements less than $\lambda$.

In some embodiments, the array length may be determined to ensure that the focusing effect counterbalances the attenuation in the tissue. In other words, the self-focus distance is such that the focusing effect approximately cancels the tissue attenuation at the distance desired for the insonation volume, producing the quasi-uniform of intensities (e.g., therapeutic range). The configuration requires the transducer spacings (the space between adjacent transducer segments in the transducer array) to be less than a wavelength $\lambda$, where the spacing may be measured by the distance along the axis of the catheter between the centers of two adjacent transducer segments.

The embodiments described above are further described with non-limiting examples herein. As the brain is approximately 14 cm wide, a cylindrical volume of therapeutic intensity of 14 cm diameter could treat a significant section of the brain. For a cylindrical volume with radius 7 cm, the array length (neglecting attenuation) can be initially estimated as a function of the self focus point SF and the wavelength $\lambda$ according to Eq. (2):

$$L_a = (SF * 4 * \lambda)^{1/2} \qquad (2)$$

This yields, for 70 mm SF at a perpendicular distance from the axial center of the array and nominal 1 mm $\lambda$ (corresponding to 1.5 MHz in brain tissue), an array $L_a$ of 17 mm. Using the known a for brain tissue $\alpha=0.004/\text{MHz/mm}$ and Eq. (1), the ultrasonic field can be calculated.

Figure 3:
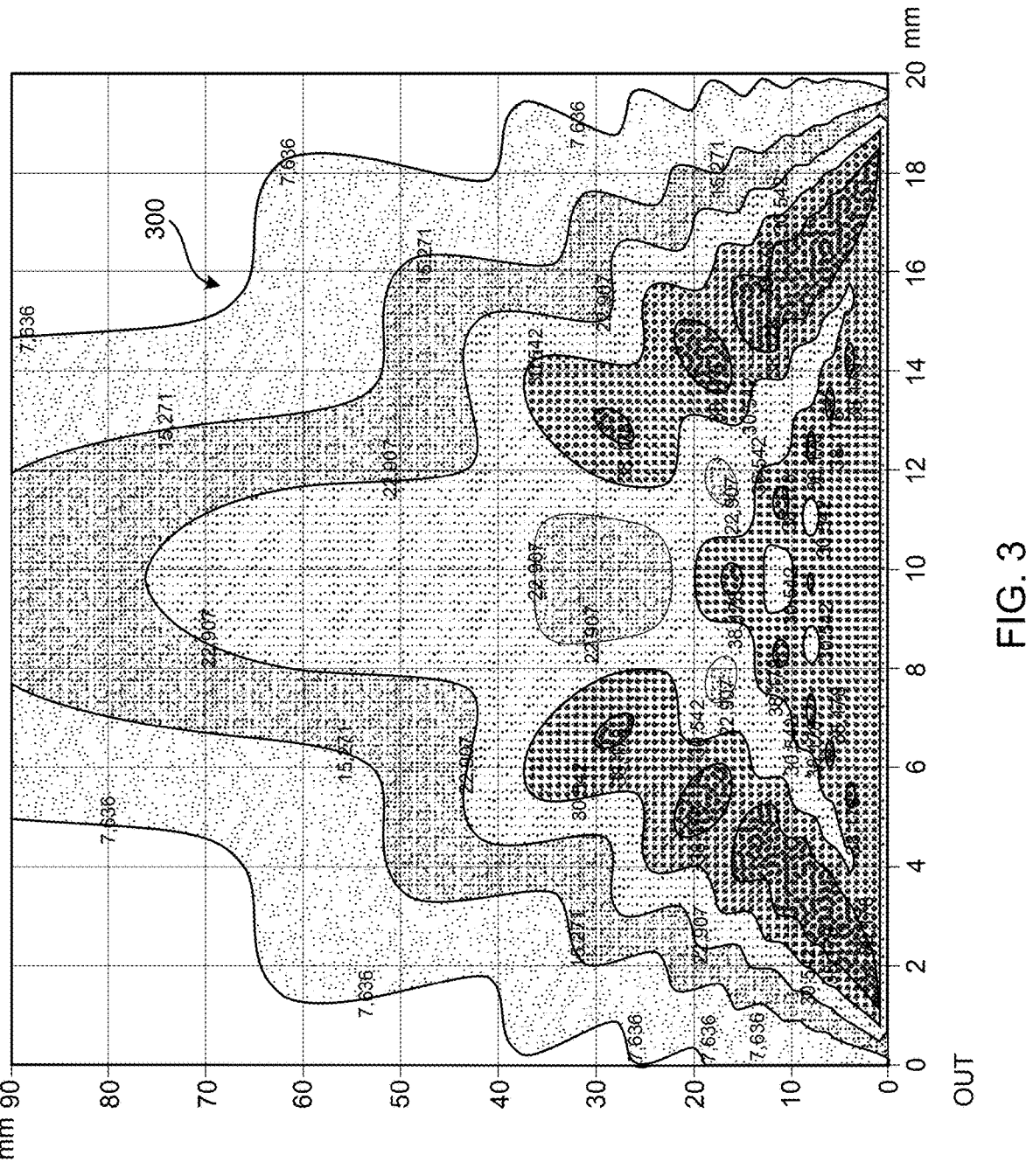
FIG. 3 is a contour plot illustrating the intensity in a longitudinal slice of the cylindrical volume surrounding the array of FIG. 1 when all the transducers are driven in parallel with unit intensity and in a certain attenuating medium, according to some embodiments.

In the example shown, the attenuation reduces the intensity such that the therapeutic range is much less than 7 cm. As the attenuation is proportional to frequency ($10^{-\alpha f d}$), a smaller (lower) frequency will reduce the attenuation and/or a longer array can be used to obtain a desirable intensity pattern. For example, at $\lambda=2$ mm (0.75 MHz) which has been frequently used in BBBO, and with a slightly longer array length of 19.8 mm, the intensity pattern is calculated as shown in FIG. 3. In the top of FIG. 3, at a distance about 7 cm, quasi-uniform intensity is shown.

Now that the A has been determined, the array of FIG. 1 can be configured. As noted, the width of the ring transducers should be small compared to the wavelength. For example, 0.1 mm width ($0.05\lambda$) of rings may be used. Similarly, it was noted that spacing should be less than a wavelength. For example, a spacing of 0.2 mm ($0.1\lambda$) among adjacent ring segment centers may be used. This results in an array of 100 transducers in an array length about 19.8 mm. Note that narrow ring transducers with spaces between them make it easier for the transducer array to be curved to follow blood vessel geometry.

Figure 2B:
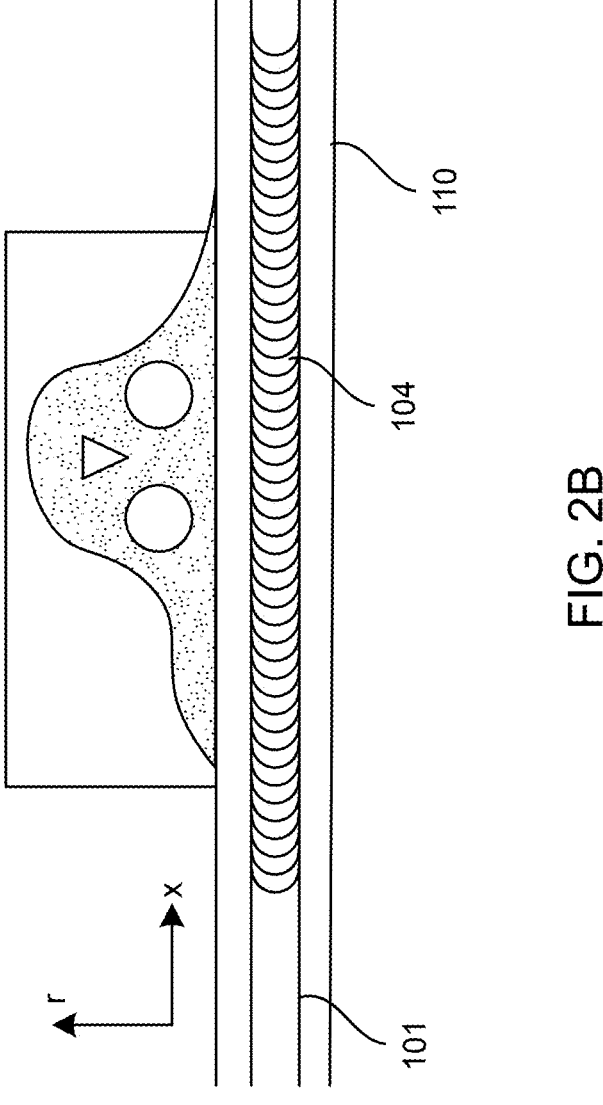
FIG. 2B illustrates a longitudinal slice through the field produced by a device shown in FIG. 1 in a vein, showing the shape of the therapeutic intensity that falls in the therapeutic range (between the maximum and the half-maximum in the field), according to some embodiments.

To show the ultrasound intensity field of the transducer array as configured above and further herein, FIG. 2B illustrates a longitudinal slice through the field. The intensity may be produced by a device shown in FIG. 1 (e.g., catheter 101, transduce array 104) in a vein 110. In FIG. 2B, the dotted shaded area shows the shape of the therapeutic intensity (e.g., between maximum and half of maximum of intensity) as a function of distance along the x and r axes. It is appreciated that FIG. 2B shows only half slice on one side of the transducer array; this pattern is found in every longitudinal slice along the axis of the catheter.

Figure 2C:
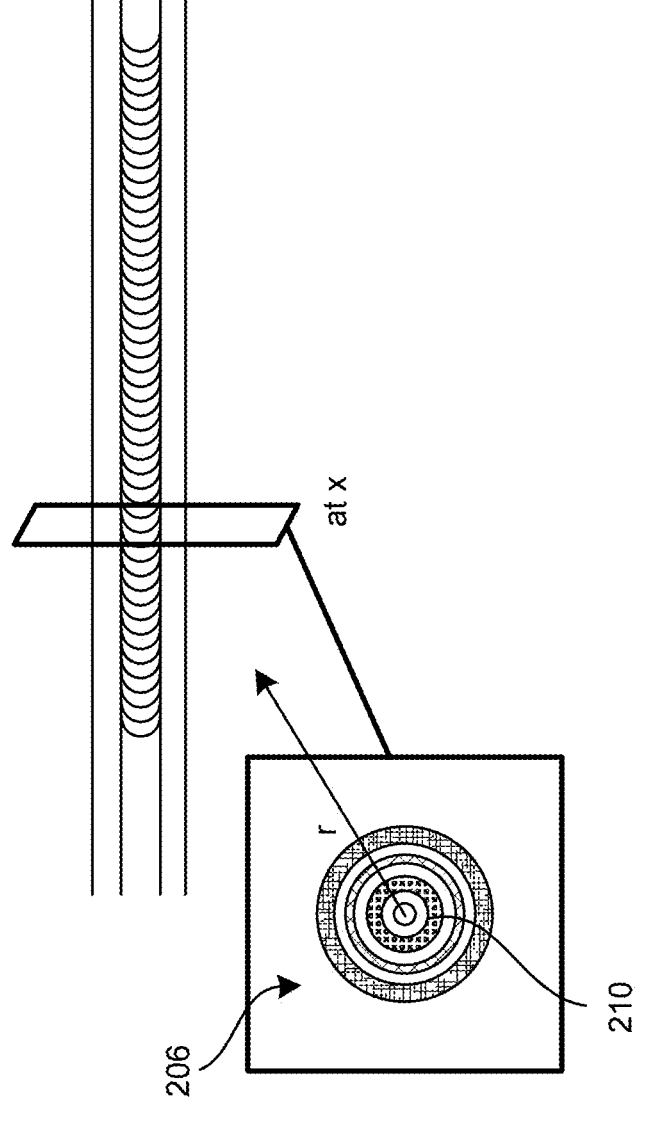
FIG. 2C illustrates an axial slice of the cylindrical, rotationally symmetric field produced by the linear array of rotationally symmetric transducers of FIG. 1, according to some embodiments.

FIG. 2C illustrates an axial slice of the cylindrical, rotationally symmetric field 206 produced by the linear array of rotationally symmetric transducers, showing how the intensity changes with the distance from the axis of linear array, r, according to some embodiments. As shown, the catheter 210 in the center and multiple "layers" in different colors (grayscales) show the intensities at different levels. As shown in FIG. 2C, an advantage of a ring transducer is that it produces an ultrasound field that is rotationally symmetric about the axis of the catheter, which exists uniformly in angle around the transducer, forming a cylindrical volume. This ultrasound field can be represented in cylindrical coordinates, radius r and axial distance, x.

FIG. 3 illustrates the intensity in a longitudinal slice of the cylindrical volume surrounding the array of FIG. 1 when all the transducers are driven in parallel with unit intensity and in a certain attenuating medium, according to some embodiments. In this longitudinal slice, the horizontal axis is the distance along the array and the vertical axis is the radial distance from the array axis. In this example, the ultrasonic intensity field is produced from a ring transducer array having a 19.8 mm array of 99 transducers excited simultaneously at an amplitude of one volt. The operating frequency used is 750 KHz (corresponding to a $\lambda$ of 2 mm in tissue), at a spacing of transducers of 0.2 mm whereas the driving signal amplitude is one volt, the brain tissue attenuation is 0.8 dB/cm/MHz. In FIG. 3, intensity is shown within the contours and the max intensity in entire volume is 45.8.

Figure 4:
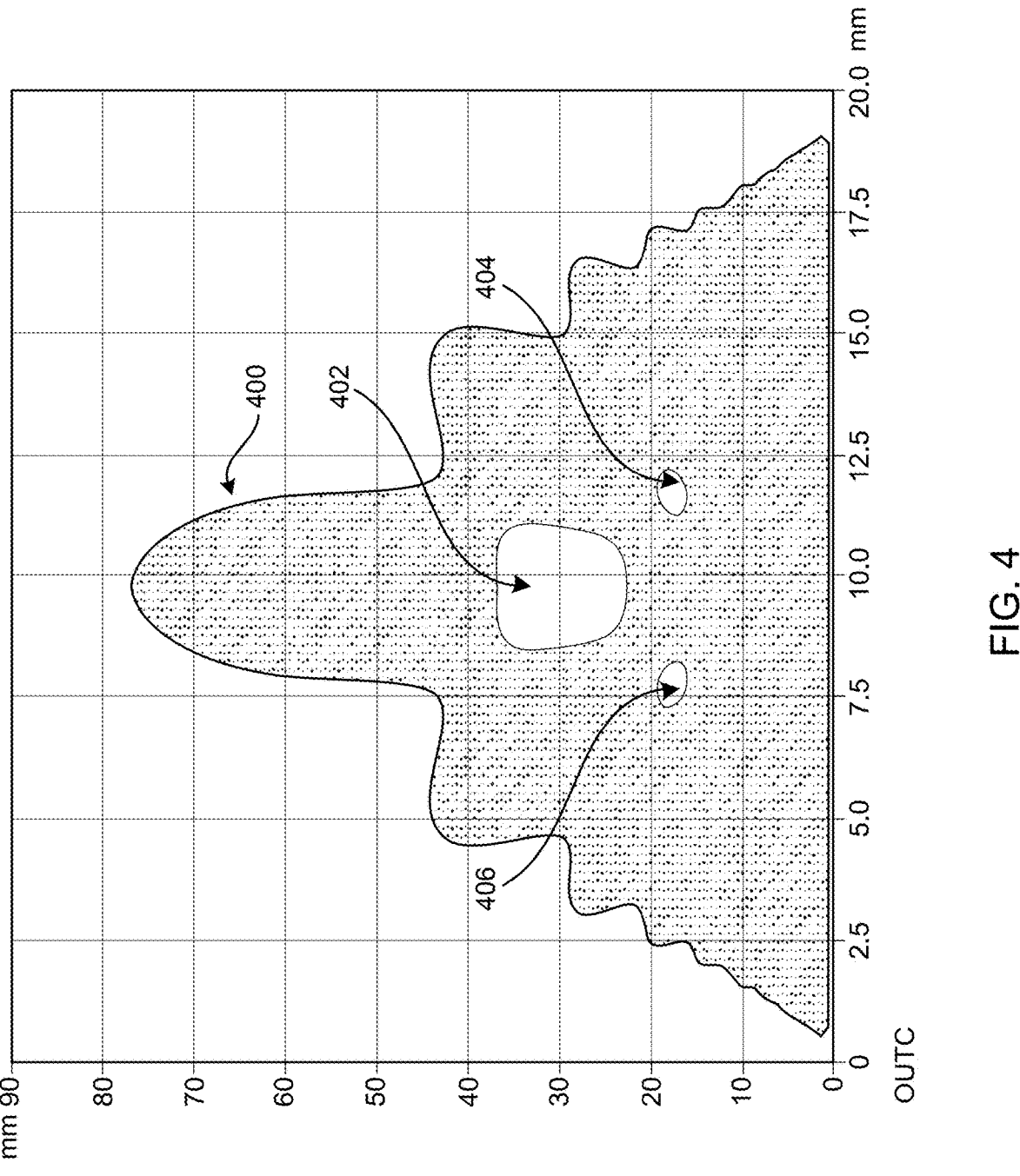
FIG. 4 illustrates a binarized intensity plot of FIG. 3, in which the gray areas indicate where the intensities in FIG. 3 fall in the therapeutic range (between the maximum and the half-maximum in the field), and the "holes" indicate where the intensities fall below the therapeutic range.

FIG. 4 illustrates a binarized intensity plot 400 of FIG. 3, in which gray areas indicate where the intensities in FIG. 3 fall in the therapeutic range (between the maximum 45.8, and half-maximum, 22.9 in the field), with the "holes" (e.g., 402, 404, 406) indicating where the intensities fall outside therapeutic range. This was done by finding the maximum value in the field in FIG. 3 and dividing all the values in the field by that maximum, recognizing that values above 0.5 correspond to the therapeutic range, so gray areas e.g., 400 indicating regions in the therapeutic range are obtained in FIG. 4.

With reference to FIGS. 3 and 4, whereas the volume of the therapeutic volume shown is large, e.g., greater than 100 mL (shown in FIG. 4), there are regions below the therapeutic range (seen as "holes" in FIG. 4). This is unacceptable for some clinical applications such as treating cancerous tumors, where tissue volumes with intensity outside the therapeutic range for BBBO would be left untreated. Accordingly, techniques have been developed to spatially move the catheter or apply selective excitation pulses to the transducer array to eliminate these "holes" (i.e. non-therapeutic intensity regions) in the "near field" to achieve quasi-uniform ultrasound intensity. Some such techniques are further described with reference to FIGS. 5-9.

Figure 5:
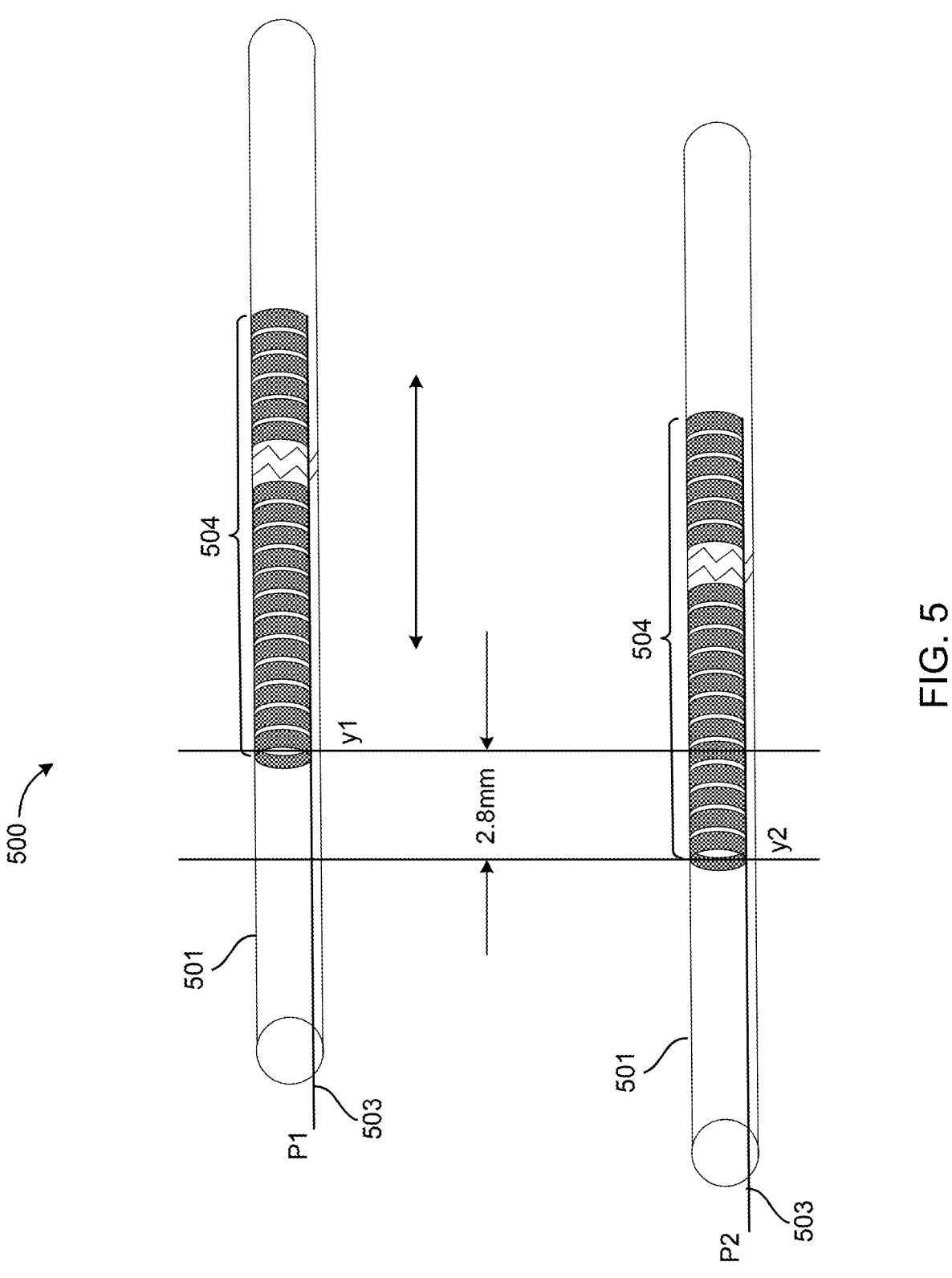
FIG. 5 illustrates movement of the catheter of a transducer device to provide a shift of 2.8 mm to eliminate "holes" in intensity in the "near field" shown in FIG. 4, according to some embodiments.

FIG. 5 illustrates spatial movement of a transducer device 500 to produce a spatial shift, according to some embodiments. In this embodiment, transducer device 500 may implement the transducer device 100 in FIG. 1 disposed on catheter 501. Transducer array 504 may be driven by excitation cable 503. As shown, the catheter 501 may be moved to carry the transducer array 504 from position y1 to position y2. The catheter 501 may be physically moved manually by an operator, for example. At position y1, the transducer array 504 may be energized by a pulse P1 via cable 503. At position y2, the transducer array 504 may be energized again by a pulse P2 by cable 503. The total therapeutic volume is 165 mL. This pattern may be repeated as the catheter and the transducer array 504 moves back and forth between positions y1 and y2.

In the example in FIG. 5, the distance between positions y1 and y2 is about the size of the hole in FIG. 4. For example, here the shifting distance between positions y1 and y2 is about 2.8 mm. It is appreciated that any suitable distance may be possible. In some embodiments, the rate in which the catheter is moved may depend on therapeutic needs.

In some examples, the ultrasound intensity (e.g., as shown in FIG. 4) may be evaluated to determine whether the ultrasound intensity in the volume at the target region where tissue is to be treated would have at least one area not within the range between the maximum intensity and half of the maximum intensity. In response to determining that the ultrasound intensity in the volume at the target region would have at least one area not within the range between the maximum intensity and half of the maximum intensity, the spatial movement may be performed simultaneously with exciting the linear transducer array.

Figure 6:
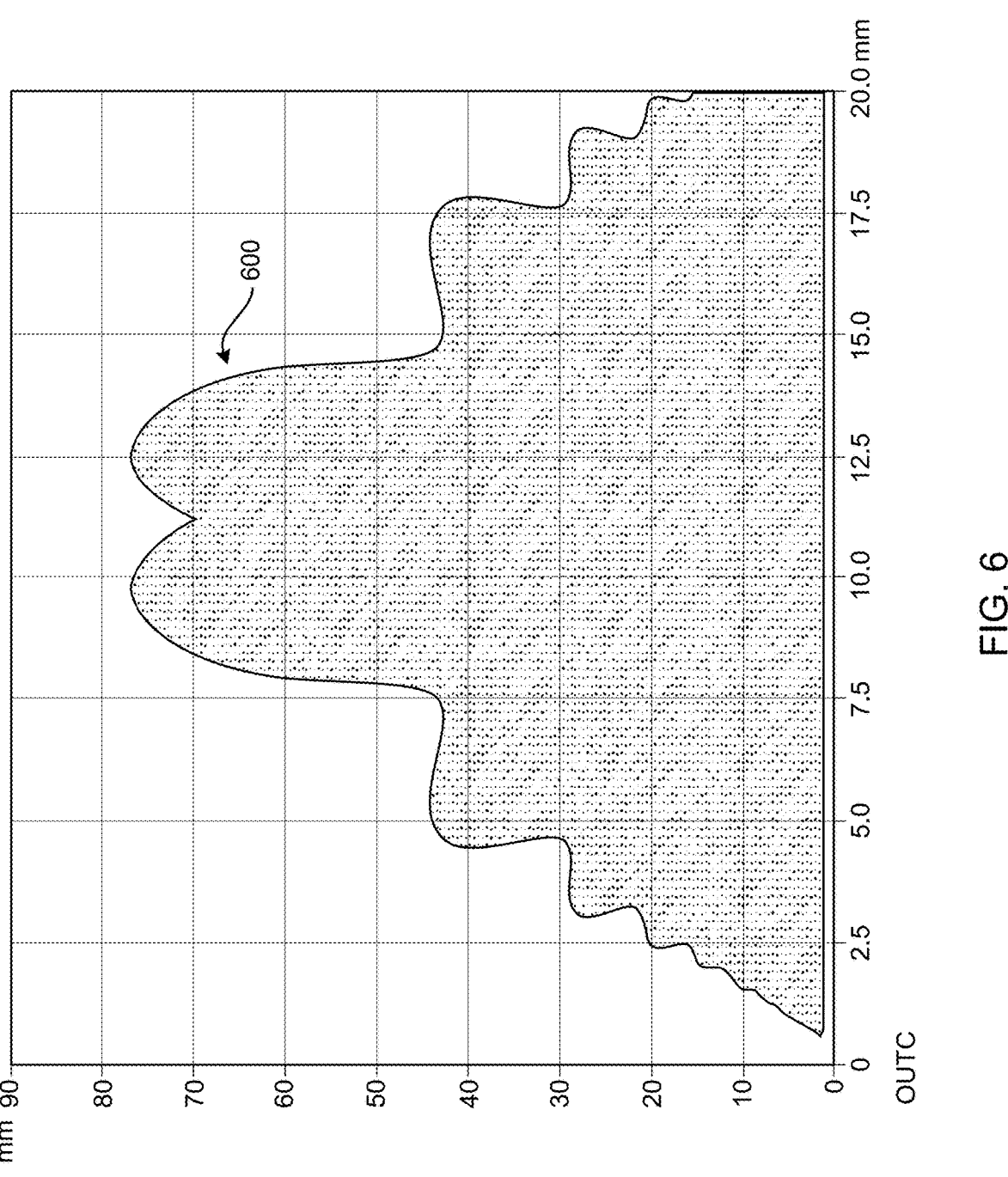
FIG. 6 illustrates a binarized intensity plot in which "holes" have been eliminated as a result of two excitations of a linear array when the array is moved axially 2.8 mm between the two excitations in a manner according to FIG. 5.

FIG. 6 illustrates an intensity plot 600 in which "holes" are eliminated as a result of two excitations of the linear array when the array is moved axially 2.8 mm between the two excitations in the manner according to FIG. 5. In non-limiting examples, the catheter may be moved by the size of the largest "hole" (e.g., 402 in FIG. 4), e.g., 2.8 mm to repeat the ultrasound exposure. In FIG. 6, the resulting "slice" in the treated volume shows that the effective treatment volume is now continuous. In some embodiments, repeated movement of the catheter can generate still larger volumes. For example, if repeated seven times, the total treated volume would be 460 mL, or approximately one-third of the total volume of the brain.

Figure 7:
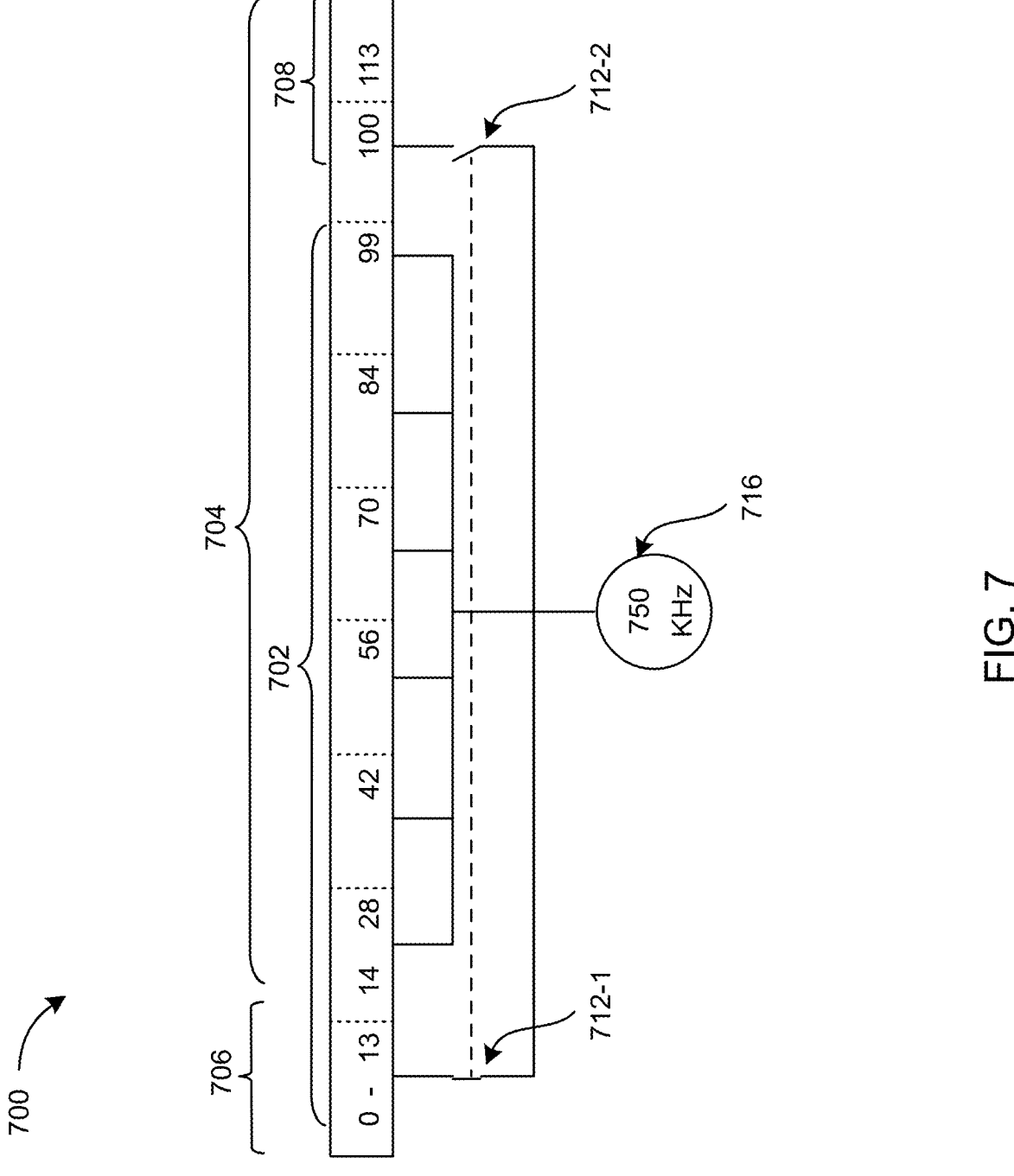
FIG. 7 illustrates an example of applying selective excitation pulses in which two groups of transducers are excited alternately, according to some embodiments.

FIG. 7 illustrates an example of applying selective excitation pulses electronically, where two groups of transducers are excited alternately. In the schematic diagram shown in FIG. 7, a transducer array 700 may implement the transducer array 104 in FIG. 1. The use of selective excitation pulses may be determined in a similar manner as method in FIG. 5 is determined. For example, the ultrasound intensity (e.g., as shown in FIG. 4) may be evaluated to determine whether the ultrasound intensity in the volume at the target region where tissue is to be treated would have at least one area not within the range between the maximum intensity and half of the maximum intensity. In response to determining that the ultrasound intensity in the volume at the target region would have at least one area not within the range between the maximum intensity and half of the maximum intensity, selective excitation pulses may be applied when exciting the linear transducer array.

Transducer array 700 may include two overlapping groups 702, 704 shifted from each other by a distance, e.g., in this case 2.8 mm along the axis of the catheter, which may be similarly determined based on the size of the "hole" or the size of a largest "hole" in the ultrasound intensity (e.g., as shown in FIG. 4). Each of the overlapping groups may include a plurality of consecutive transducers. For example, group 702 may include 100 transducers 0-99, whereas group 704 may include transducers 14-113. (Note the 14-segment "offset" produces the desired 2.8 mm spatial displacement.)

In some embodiments, a portion of the first group 702 (e.g., portion 706, including transducers 0-13) that is non-overlapping with the second group 704 may be coupled to a switch 712 that is coupled to an excitation source 716. A portion of the second group 704 (e.g., portion 708, including transducers 100-113) that is non-overlapping with the first group 702 may be coupled to the switch 712, where the switch 712 may be configured to operate in a first state and a second state. In the first state, the switch 712 may connect the exciting source 716 to the transducer group 706, at 712-1. In the second state, the switch 712 may connect the exciting source 716 to the transducer group 708, at 712-2.

The other portions of the groups 702, 704 (e.g., overlapping portion, transducer 14-99) may be constantly coupled to the excitation source 716, without a switch.

In non-limiting examples, switch 712 may be double-throw switch, e.g., a single-pole-double-throw (SPDT) switch. Switch 712 may be a DPDT switch. In some examples, switch 712 may be a multiplexer that can be manufactured in a semiconductor chip. In such configurations, a single cable can be used to drive the various transducers in the transducer array. It is appreciated that other switching devices may be used.

In operation, the portions 706 and 708 may be alternately excited by the excitation source 716. For example, switch 712 may be switched to a first state to provide a first excitation pulse to transducers in portion 706 from the excitation source, with the transducers in portion 708 being disconnected from the excitation source 716. At this time, the first excitation pulse is also applied to transducers 14-99. Then, switch 712 is switched to a second state to provide a second excitation pulse to transducers in portion 708 with the transducers in portion 706 being disconnected from the excitation source 716, whereas transducers 14-99 are also driven by the second excitation pulse. In some embodiments, this process repeats, whereas switch 712 operates between the first state and the second state. In this manner, overlapping transducer groups 702 and 704 are alternately driven by the first excitation pulse and the second excitation pulse.

In some embodiments, with the spacing of transducers being 0.2 mm, two overlapping groups of 100 transducers (e.g., transducers 0-99, or transducers 14-113) form two apertures of 19.8 mm (99 spacings) each, shifted by 2.8 mm (14×0.2 mm). When alternating excitation pulses are applied to the two overlapping groups of transducers, such action effectively "moves" the apertures by 2.8 mm along the axis of the catheter. Although not shown, the configuration in FIG. 7 may generate an ultrasound intensity field as similarly shown in FIG. 6, showing that quasi-uniform intensity can be achieved in the "near field."

In various configurations, the alternating rate between sequential pulses respectively applied to transducers in portions 706 and 708 may be configured in a similar manner as described in embodiments in FIG. 5. As similar with configuration shown in FIG. 5, different ultrasonic volumes can be obtained for different anatomical applications. Further, the overlapping grouping of transducers as shown in FIG. 7 provides the advantages of reduced number of transducers and thus saving of space.

In some embodiments, the speed of switching between the first state and the second state for switch 712 may depend upon the ultrasound and drug dose needed. For example, if the drug quickly penetrates into the tissue that is insonated the new field needed to ensure uniform dose can be quickly applied (at a higher speed of switching). If not, a longer insonation at each array "position" would be required (at a lower speed of switching).

Figure 8:
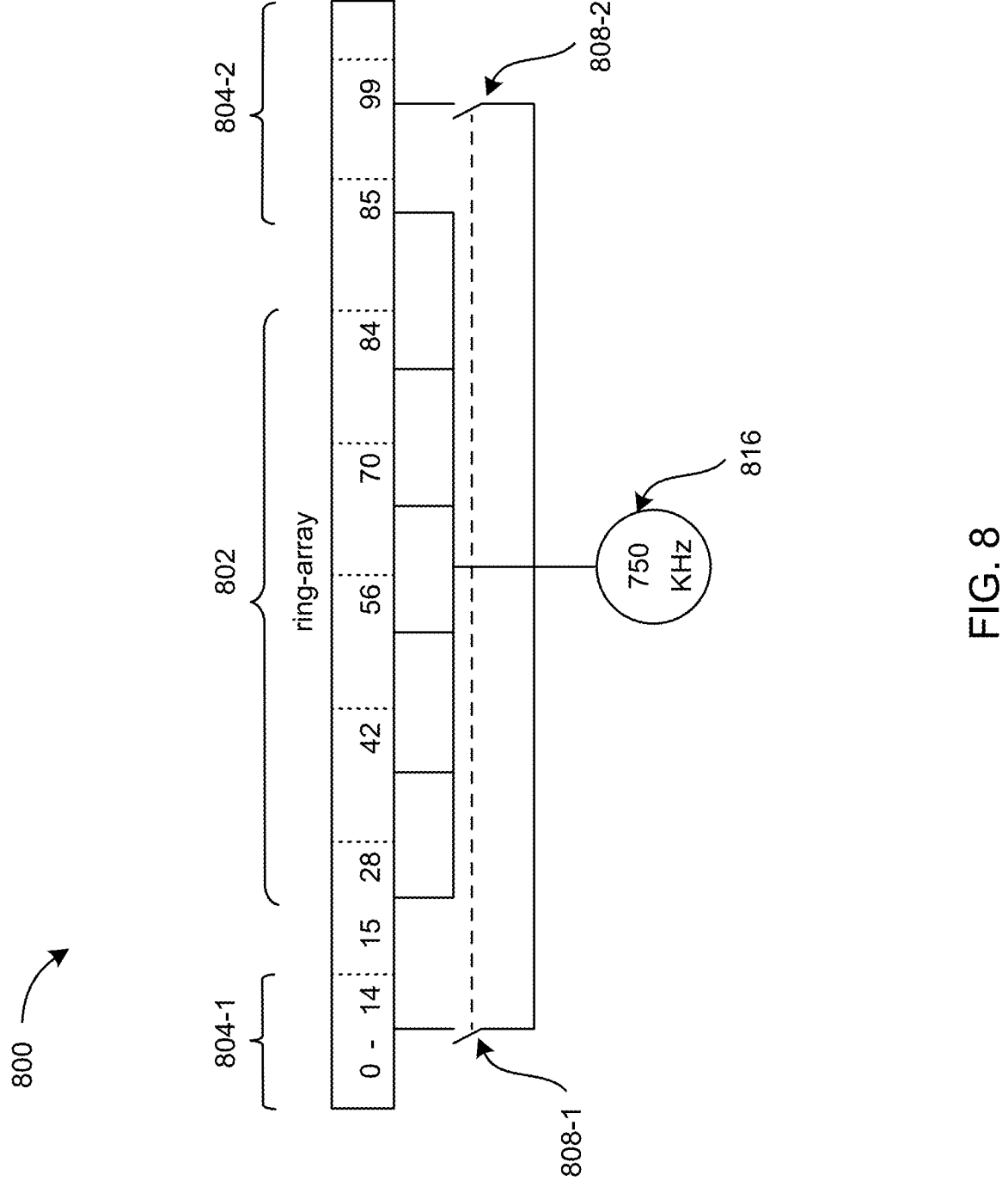
FIG. 8 illustrates another example of applying selective excitation pulses in which two groups of transducers are excited alternately, according to some embodiments.

FIG. 8 illustrates another example of applying selective excitation pulses in which two groups of transducers are excited alternately, according to some embodiments. In the schematic diagram shown in FIG. 8, a transducer array 800 may implement the transducer array 104 in FIG. 1. The use of selective excitation pulses in FIG. 8 may be determined in a similar manner as described in FIGS. 5 and 7. For example, the ultrasound intensity (e.g., as shown in FIG. 4) may be evaluated to determine whether the ultrasound intensity in the volume at the target region where tissue is to be treated would have at least one area exceeding a range between the maximum intensity and half of the maximum intensity. In response to determining that the ultrasound intensity in the volume at the target region would have at least one area exceeding the range between the maximum intensity and half of the maximum intensity, selective excitation pulses may be applied when exciting the linear transducer array.

Transducer array 800 may include two non-overlapping transducer groups 802, 804. Transducer group 804 may include two subgroups 804-1, 804-2, in which transducer group 802 is sandwiched. Each group or subgroup may include a plurality of consecutive transducers. For example, subgroup 804-1 may include transducers 0-14; subgroup 804-2 may include transducers 85-99; and group 802 may include transducers 15-84, where the length of transducers 0-14 and 85-99 will each give 2.8 mm, which may be similarly determined based on the size of the "hole" or the size of a largest "hole" in the ultrasound intensity (e.g., as shown in FIG. 4).

In some embodiments, transducers in transducer group 804 may be coupled to an excitation source 816 to receive a driving signal via a switch 808, whereas transducers in transducer group 802 may be constantly coupled to the excitation source 816. In some examples, switch 808 may be a double-pole switch with the two poles 804-1 and 804-2 operating to turn on and off groups 804-1 and 804-2 simultaneously.

In operation, the two transducer groups 802, 804 (including 804-1, 804-2) may be alternately excited by the excitation source 816. For example, a first excitation pulse is provided to transducer groups 802 and 804 (e.g., transducers 0-99) with switch 808 being turned-on. Alternately, a second excitation pulse is provided to the center transducer group 802 only, with switch 808 being turned-off. In this manner, the transducers in group 802 and 804 (e.g., transducers 0-99) are connected to a first excitation pulse; then the transducers in group 804 (e.g., transducers 0-14 and 85-99) are disconnected, leaving the transducers in the center group 802 (e.g., transducers 15-84) continuing to be driven by a second excitation pulse. In some examples, this process may be repeated.

Figure 9A:
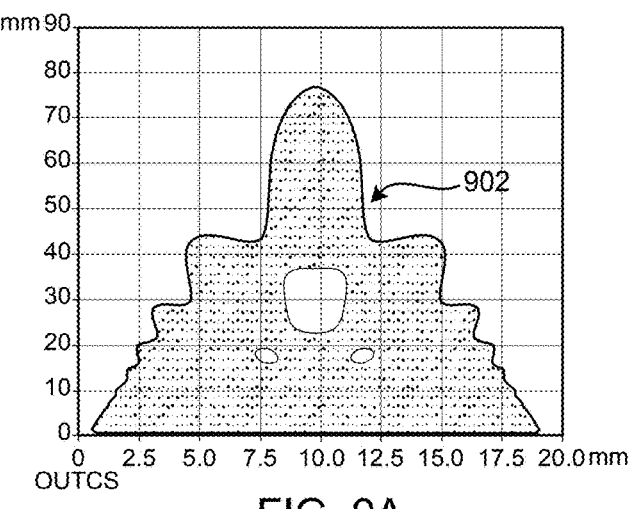
FIGS. 9A-9C illustrate intensity plots in which "holes" have been eliminated as a result of energizing one subsection of a transducer array alternately with another in a manner according to FIG. 8.
Figure 9B:
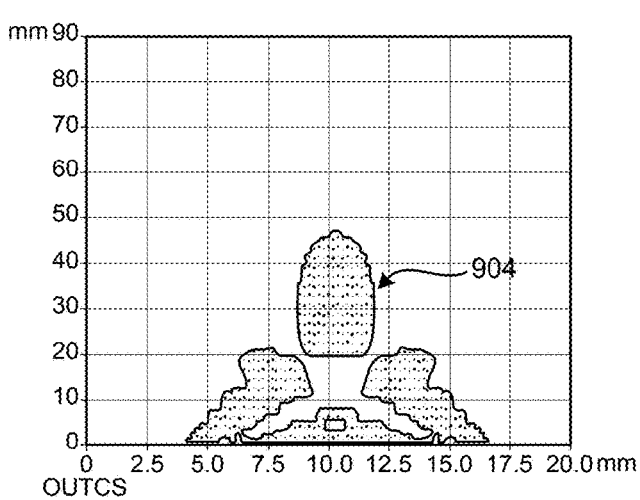
Figure 9C:
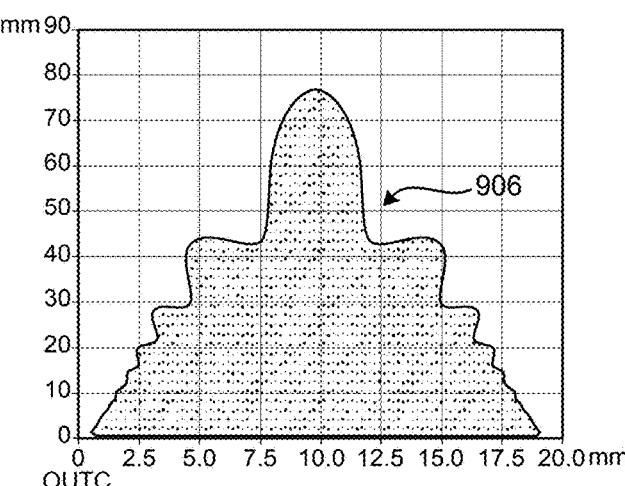

In comparison to embodiments in FIG. 7, the transducer array 800 in FIG. 8 is operated to have two completely overlapping transducer groups (e.g., the full array and center array within the full array) alternately excited. FIGS. 9A-9C illustrate intensity plots in which "holes" can be eliminated as a result of energizing a subsection of the array in a manner according to FIG. 8. For example, FIG. 9A illustrates therapeutic intensity regions 902 produced from a full transducer array as similarly shown in FIG. 4. FIG. 9B illustrates therapeutic intensity regions (904 in gray) produced from central 70 transducers (transducer group 802 in FIG. 8) driven at 80% of the amplitude of the driving signal for the full array. FIG. 9C illustrates total insonation from the sum of two excitations applied to the full array and the center array, respectively. As shown in the intensity plot 906 in FIG. 9C, the "holes" can be eliminated, resulting in quasi-uniform intensity in the "near field."

Similar to the configuration shown in FIG. 7, long array of transducers in FIG. 8 may be energized at a time with appropriate switching and can therefore insonate large volumes of tissue with only one signal cable connected to the excitation source. In various configurations, the alternating rate between sequential excitation pulses respectively applied to transducer groups 802 and 804 may be configured in a similar manner as described in embodiments in FIGS. 5 and 7.

Returning to FIG. 1, in some variations, a continuous "stripe" ultrasound transducer, in which transducer segments 104-*n* touch each other may be possible. The calculation in Eq. (1) can also be applied to the continuous (stripe) transducers where the transducer is modelled by many close point transmitters along its length, and the spacing of the transducers can be zero. However, such a configuration would be much less flexible for insertion into the circulatory system and the hole-filling techniques described could not be implemented.

Figure 10:
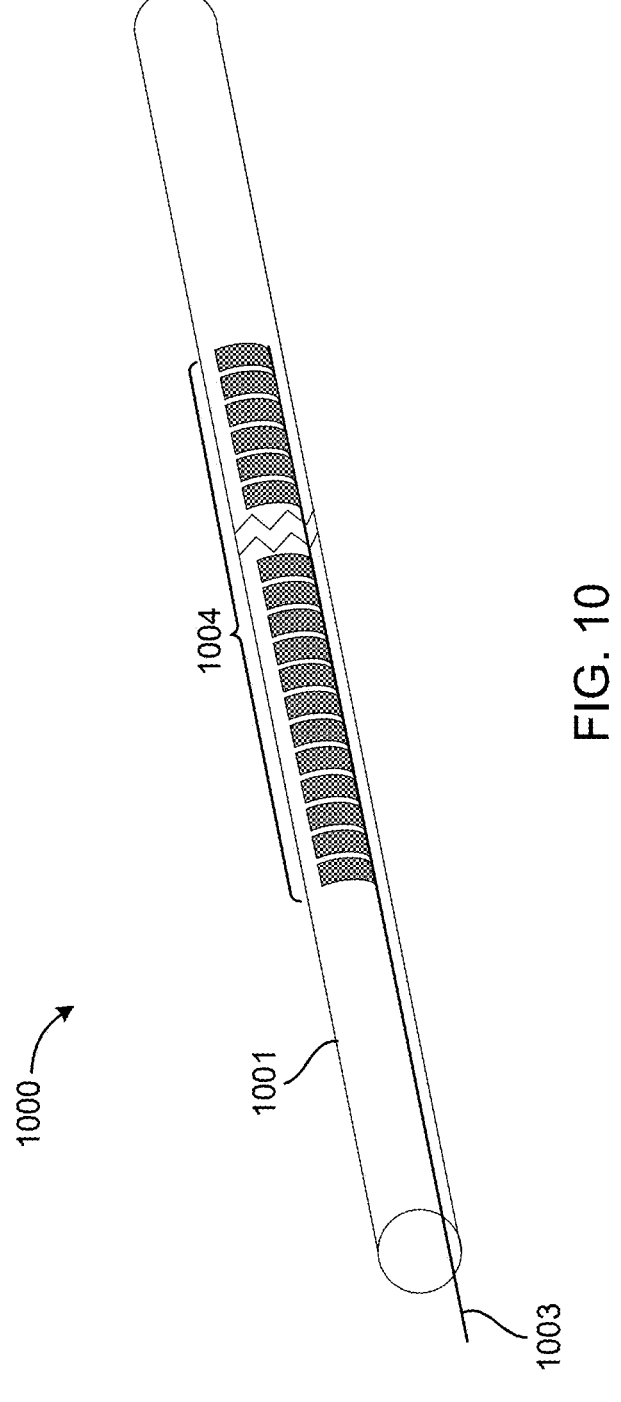
FIG. 10 shows a variation of a transducer device having a linear array of partial ring transducers, according to some embodiments.

In other variations, FIG. 10 shows a transducer device 1000 having a linear array of partial ring transducers 1004, according to some embodiments. The transducer array 1004 is similar to transducer array 104 (FIG. 1) with the difference being that each of the transducer segments is partially wrapped, instead of fully wrapped around the circumference of the catheter 1001. The transducers 1004 can be configured in a similar manner as the transducer array described in FIG. 1. For example, the transducer segments may each have a width much less than a wavelength wide (at their frequency of operation). The various selective excitation methods as described in FIGS. 5, 7 and 8 may also be applied to the transducer device in FIG. 10. The configuration in FIG. 10 would generate an ultrasound intensity field similarly to that shown in FIG. 2C but only a partial cylinder in the region facing the active part of the transducers, i.e., not completely rotationally symmetric about the axis of the catheter, but rather a fan-shape.

In some embodiments, the transducer rings 1004 may be spaced at less than a wavelength apart (measured by the distance along the axis of the catheter between the centers of two adjacent transducer rings). In some embodiments, the transducer rings may be made of any of the well-known ultrasound transducer types or later developed, e.g. PZT, CMUT, PVDF-TrFE, etc. For example, the transducers may be thin film plastic transducers because they are light and flexible. This structure as described above and further herein produces a cylindrical volume of quasi-uniform ultrasound intensity that may be useful, e.g. for opening the blood-brain barrier in brain tissue when combined with microbubbles, as described above and further herein.

Having described embodiments in FIGS. 1-10, it is appreciated that a method for ultrasound therapy may include inserting the transducer array such as what is described in FIGS. 1 and 10 into a body lumen using a catheter. When the transducer reaches near the tissue to be treated, the transducer can be excited with shifting excitation pulses, e.g., by moving the catheter back and forth, or alternately exciting excitation pulses respectively for different groups of transducers, where the different groups of transducers may be arranged overlapped with a distance along the axis of the catheter. In some embodiments, the catheter may also carry lumens for injecting therapeutic agents or identifying agents, e.g., radiologic contract media. In some embodiments, the catheter may also carry additional ultrasound receivers to monitor the ultrasound intensity on the microbubbles, where higher-than-needed intensities may produce undesirable inertial cavitation of these bubbles which produces distinctive frequencies. When such frequencies are detected by these monitoring transducers, the drive power can be reduced to eliminate inertial cavitation.

The embodiments described above provide advantages over existing systems in ultrasound therapy. Self-focusing is a known characteristic arising from constructive interference from different areas of an active aperture. The near-field self-focusing region is almost always avoided in existing systems because of the heterogeneity of intensity in the near field. For the important use of an acoustic fields for opening the blood-brain barrier, previous research employed focused ultrasound and showed safe BBB-opening occurred over a two-to-one range of acoustic intensity. In the present disclosure, a useful part of the array's insonated volume is where the intensity lies between the maximum in the total acoustic field and one-half of that maximum.

The systems and methods as described in the present disclosure illustrate how a linear array of ultrasound transducers driven simultaneously at the same frequency may achieve "self-focusing." Focusing ultrasound increases its intensity, e.g., in the way a lens acts as a "burning glass," whereas tissue attenuation, generally proportional to frequency, decreases ultrasound intensity. By balancing the focusing increase in the intensity with the tissue-attenuating decrease in the intensity at the focus distance, a quasi-uniform (e.g., at two-to-one range) ultrasound intensity can be attained.

Various embodiments described above and shown in the figures show embodiments of a device to produce BBBO insonation volumes and uses thereof. It is appreciated that other uses of this device, for example deep brain stimulation or for sonobiopsy, may also be possible. Further, it is appreciated that the self-focusing point and the ultrasound field related to it depend on the wavelength, $\lambda$, so changing the wavelength may also make the ultrasound field more uniform.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

The invention claimed is:

1. A method for providing insonation volume in ultrasound therapy treating tissues at a target region, wherein the tissues have an attenuation constant, the method comprising:

using a catheter to introduce a linear transducer array into a body lumen to treat the tissues, the linear transducer array comprising a plurality of equally spaced transducer segments;

causing to determine an operating frequency for exciting the linear transducer array and a length of the linear transducer array to be excited by:

determining a self focus distance from an axial center of the linear transducer array based on a size of the target region;

determining an initial transducer length as a function of an initial wavelength and the self focus distance, wherein the initial transducer length is proportional to a square root of the self focus distance multiplied by the initial wavelength;

determining the length of the linear transducer array to be excited as the initial transducer length;

determining the operating frequency as corresponding to the initial wavelength; and calculating ultrasound intensity in the target region by adjusting the length of the linear transducer array and the operating frequency such that the ultrasound intensity in the target region is within a desirable intensity pattern, wherein the ultrasound intensity in the target region is calculated based at least in part on the attenuation constant of the tissues, the operating frequency, and the length of the linear transducer array; and causing to excite the length of the linear transducer with a signal at the operating frequency to produce ultrasound intensity in the target region.

2. The method of claim 1, further comprising:

determining whether the ultrasound intensity in a volume at the target region would have at least one area not within a range between a maximum intensity and a half of the maximum intensity; and in response to determining that the ultrasound intensity in the volume at the target region would have at least one area not within the range between the maximum intensity and the half of the maximum intensity:

spatially moving the catheter axially by an offset after exciting the linear transducer array; and exciting the linear transducer array a second time after spatially moving the catheter.

3. The method of claim 2, further comprising:

determining the offset based on a size of the at least one area in which the ultrasound intensity is not within the range between the maximum intensity and the half of the maximum intensity.

4. The method of claim 1, further comprising:

determining whether the ultrasound intensity in the target region would have at least one area not within a range between a maximum intensity and half of the maximum intensity; and in response to determining that the ultrasound intensity in the target region would have at least one area not within the range between the maximum intensity and half of the maximum intensity, exciting the length of the linear transducer with the signal at the operating frequency by applying, via a cable coupled to the plurality of transducer segments, selective excitation pulses of the signal to the plurality of transducer segments.

5. The method of claim 4, wherein applying the selective excitation pulses of the signal comprises:

applying a first excitation pulse of the signal to a first group of consecutive transducer segments in the linear transducer array; and alternately applying a second excitation pulse of the signal to a second group of consecutive transducer segments in the linear transducer array;

wherein the first group of consecutive transducer segments and the second group of consecutive transducer segments are overlapping and spatially shifted at an offset from each other along an axial direction of the catheter.

6. The method of claim 5, further comprising:

determining the offset based on a size of the area in which the ultrasound intensity is not within the range between the maximum intensity and half of the maximum intensity.

7. The method of claim 5, wherein:

applying the first excitation pulse of the signal comprises causing at least one switch coupling an excitation source to the linear transducer array to operate at a first state to provide the signal from the excitation source to the first group of consecutive transducer segments in the linear transducer array; and applying the second excitation pulse of the signal comprises causing the at least one switch to operate at a second state to provide the signal from the excitation source to the second group of consecutive transducer segments in the linear transducer array.

8. The method of claim 7, wherein:

the first group of consecutive transducer segments comprise a first portion of consecutive transducer segments and a second portion of consecutive transducer segments;

the second group of consecutive transducer segments comprise the second portion of consecutive transducer segments and a third portion of consecutive transducer segments; and the at least one switch is configured to operate at the first state to couple the excitation source to the first portion of consecutive transducer segments while disconnecting the third portion of consecutive transducer segments from the excitation source, and at the second state to couple the excitation source to the third portion of consecutive transducer segments while disconnecting the first portion of consecutive transducer segments from the excitation source;

wherein the second portion of consecutive transducer segments are constantly coupled to the excitation source.

9. The method of claim 4, wherein applying the selective excitation pulses of the signal comprises:

applying a first excitation pulse of the signal to a first group of consecutive transducer segments in the linear transducer array; and alternately applying a second excitation pulse of the signal to a second group of consecutive transducer segments in the linear transducer array;

wherein the first group of consecutive transducer segments encompass the second group of consecutive transducer segments along an axial direction of the catheter.

10. The method of claim 9, wherein the first group of consecutive transducer segments comprise a first portion of consecutive transducer segments, a second portion of consecutive transducer segments, and the second group of consecutive transducer segments sandwiched between the first portion of consecutive transducer segments and the second portion of consecutive transducer segments, wherein a length of the first portion of consecutive transducer segments and a length of the second portion of consecutive transducer segments are each determined based on a size of the at least one area in which the ultrasound intensity is not within the range between the maximum intensity and the half of the maximum intensity.

11. The method of claim 10, wherein:

applying the first excitation pulse of the signal comprises causing at least one switch coupling an excitation source to the linear transducer array to operate at an on state to provide the signal from the excitation source to the first portion of consecutive transducer segments and the second portion of consecutive transducer segments; and applying the second excitation pulse of the signal comprises causing the at least one switch to operate at an off state to disconnect the first portion of consecutive transducer segments and the second portion of consecutive transducer segments from the excitation source;

wherein the second group of consecutive transducer segments are constantly coupled to the excitation source.

12. The method of claim 1, wherein the desirable intensity pattern comprises an intensity range between a maximum intensity and half of the maximum intensity.

13. The method of claim 1, wherein calculating the ultrasound intensity in the target region comprises:

for each of a plurality of observation points on an observation plane in the target region, determining a respective intensity based on a square of a sum of amplitudes each contributed by a respective transducer segment of the a plurality of transducer segments in the length of the linear transducer array, wherein the amplitude contributed by the respective transducer segment is:

proportional to a transmitter amplitude of the respective transducer segment;

inversely proportional to the attenuation constant of the tissues multiplied by the operating frequency and a distance from the respective transducer segment to the observation point on the observation plane; and proportional to a distance from the axial center of the linear transducer array to the observation plane divided by a square of the distance from the respective transducer segment to the observation point on the observation plane.

14. An apparatus for providing insonation volume in ultrasound therapy treating tissues at a target region, wherein the tissues have an attenuation constant, the apparatus comprising:

a catheter having a linear transducer array disposed thereon, the catheter is configured to be introduced into a body lumen to treat the tissues, wherein the linear transducer array comprises a plurality of equally spaced transducer segments configured in a manner in which a length of the linear transducer array is excited by a signal at an operating frequency, wherein the length of the linear transducer array to be excited and the operating frequency of the signal are determined by:

determining a self focus distance from an axial center of the linear transducer array based on a size of the target region;

determining an initial transducer length as a function of an initial wavelength and the self focus distance, wherein the initial transducer length is proportional to a square root of the self focus distance multiplied by the initial wavelength;

determining the length of the linear transducer array to be excited as the initial transducer length;

determining the operating frequency as corresponding to the initial wavelength; and calculating ultrasound intensity in the target region by adjusting the length of the linear transducer array and the operating frequency such that the ultrasound intensity in the target region is within a desirable intensity pattern, wherein the ultrasound intensity in the target region is calculated based at least in part on the attenuation constant of the tissues, the operating frequency, and the length of the linear transducer array.

15. The apparatus of claim 14 further comprising a single cable coupled to the linear transducer array to provide the signal from an excitation source to excite the equally spaced transducer segments in the length of the linear transducer array simultaneously.

16. The apparatus of claim 14 further comprising a single cable configured to be coupled to an excitation source and at least one switch coupled to the single cable and the linear transducer array to provide selective excitation pulses of the signal from the excitation source to the linear transducer array.

17. The apparatus of claim 16, wherein:

the linear transducer array comprises a first portion of consecutive transducer segments coupled to the at least one switch, a second portion of consecutive transducer segments configured to be coupled to the excitation source, and a third portion of consecutive transducer segments coupled to the at least one switch; and the at least one switch is configured to operate at a first state to provide a first excitation pulse of the signal from the excitation source to the first portion of consecutive transducer segments while the third portion of consecutive transducer segments are disconnected from the excitation source, and at a second state to provide a second excitation pulse of the signal from the excitation source to the third portion of consecutive transducer segments while the first portion of consecutive transducer segments are disconnected from the excitation source.

18. The apparatus of claim 17, wherein a length of the first portion of consecutive transducer segments and a length of the third portion of consecutive transducer segments are each based at least in part on the operating frequency of the signal and the attenuation of the tissue.

19. The apparatus of claim 16, wherein:

the linear transducer array comprises a first portion of consecutive transducer segments coupled to the at least one switch, a second portion of consecutive transducer segments configured to be coupled to the excitation source, and a third portion of consecutive transducer segments coupled to the at least one switch; and the at least one switch is configured to operate at an on state to provide a first excitation pulse of the signal from the excitation source to the first portion of consecutive transducer segments and the third portion of consecutive transducer segments, and at an off state to disconnect the first portion of consecutive transducer segments and the third portion of consecutive transducer segments from the excitation source.

20. The apparatus of claim 19, wherein a length of the first portion of consecutive transducer segments and a length of the third portion of consecutive transducer segments are each based at least in part on the operating frequency of the signal and the attenuation constant of brain tissues.

21. The apparatus of claim 14, wherein the plurality of equally spaced transducer segments are each a ring wrapped around circumference of the catheter.

22. The apparatus of claim 21, wherein a width of each of the plurality of transducer segments is in a range from 0.01~0.75 times a wavelength of the signal.

23. The apparatus of claim 14, wherein the desirable intensity pattern comprises an intensity range between a maximum intensity and half of the maximum intensity.

24. The apparatus of claim 14, wherein calculating the ultrasound intensity in the target region comprises:

for each of a plurality of observation points on an observation plane in the target region, determining a respective intensity based on a square of a sum of amplitudes each contributed by a respective transducer segment of the a plurality of transducer segments in the length of the linear transducer array, wherein the amplitude contributed by the respective transducer segment is:

proportional to a transmitter amplitude of the respective transducer segment;

inversely proportional to the attenuation constant of the tissues multiplied by the operating frequency and a distance from the respective transducer segment to the observation point on the observation plane; and proportional to a distance from the axial center of the linear transducer array to the observation plane divided by a square of the distance from the respective transducer segment to the observation point on the observation plane.

* * * * *